(12) United States Patent
Carmeli et al.

(10) Patent No.: US 9,715,662 B2
(45) Date of Patent: Jul. 25, 2017

(54) INCONSISTENCY DETECTION BETWEEN STRUCTURED AND NON-STRUCTURED DATA

(71) Applicant: International Business Machines Corporation, Armonk, NY (US)

(72) Inventors: Boaz Carmeli, Koranit (IL); Ruty Rinott, Jerusalem (IL); Noam Slonim, Jerusalem (IL)

(73) Assignee: International Business Machines Corporation, Armonk, NY (US)

( * ) Notice: Subject to any disclaimer, the term of this patent is extended or adjusted under 35 U.S.C. 154(b) by 569 days.

(21) Appl. No.: 13/751,163

(22) Filed: Jan. 28, 2013

(65) Prior Publication Data
US 2014/0214732 A1   Jul. 31, 2014

(51) Int. Cl.
    *G06N 99/00*    (2010.01)
    *G06F 19/00*    (2011.01)
    *G06F 17/30*    (2006.01)

(52) U.S. Cl.
    CPC ..... *G06N 99/005* (2013.01); *G06F 17/30303* (2013.01); *G06F 19/322* (2013.01)

(58) Field of Classification Search
    CPC .................................................. G06N 99/005
    USPC .......................................................... 706/45
    See application file for complete search history.

(56) References Cited

U.S. PATENT DOCUMENTS 7,251,782 B1 *   7/2007   Albers et al. ................. 715/711
7,610,192 B1    10/2009   Jamieson
7,813,937 B1    10/2010   Pathria et al.
8,234,562 B1 *   7/2012   Evans .................. G06F 17/243
                                                         715/221
2009/0299977 A1 12/2009   Rosales

OTHER PUBLICATIONS

R. Duin, "The Combining Classifier: to Train or Not to Train?", Proc. IEEE 16th Int'l Conf. on Pattern Recognition, vol. 2, 2002, pp. 765-770.*

J. Bargas-Avila and G. Oberholzer, "Online Form Validation: Don't Show Errors Right Away", Proc. Human-Computer Interaction 2003, pp. 848-851.*

Singh et al., "Prescription Errors and Outcomes Related to Inconsistent Information Transmitted through Computerized Order-Entry: A Prospective Study", Manual detection of inconsistencies in EHR, 2009, 8 pages.

(Continued)

*Primary Examiner* — Vincent Gonzales

(74) *Attorney, Agent, or Firm* — Ziv Glazberg

(57) ABSTRACT

A computer implemented method, computerized apparatus and computer program product for inconsistency detection between structured and non-structured data. The method comprising: automatically determining, by a computer, inconsistencies between fields in electronics records, the fields comprise at least a structured field and a non-structured field, the fields are designed to be able to include overlapping information in structured and non-structured form; and indicating, by the computer, to a user potential inconsistencies. Optionally, the indication uses a visual cue when displaying the electronic record to the user, wherein the visual cue indicates the fields which are determined to comprise inconsistent content.

19 Claims, 3 Drawing Sheets

(56) References Cited

OTHER PUBLICATIONS

Tate et al., "Using free text information to explore how and when GPs code a diagnosis of ovarian cancer: an observational study using primary care records of patients with ovarian cancer", BMJ Open 2011, 2011, 7 pages.

Stein et al., "Exploring the degree of concordance of coded and textual data in answering clinical queries from a clinical data repository", Journal of the American Medical Informatics Association, vol. 7, No. 1, 2000, pp. 42-54.

Goldstein et al., "Three Approaches to Automatic Assignment of ICD-9-CM Codes to Radiology Reports", AMIA 2007 Symposium Proceedings, pp. 279-283, 2007.

Brodley et al., "Identifying Mislabeled Training Data", Journal of Artificial Intelligence Research 11, pp. 131-167, 1999.

* cited by examiner

TRAINING PHASE

INCONSISTENCY DETECTION PHASE

INCONSISTENCY DETECTION BETWEEN STRUCTURED AND NON-STRUCTURED DATA

TECHNICAL FIELD

The present disclosure relates to artificial intelligence in general, and to machine learning, in particular.

BACKGROUND

Ensuring concordance of data stored in different fields of Electronic Records (ERs), such as Electronic Health Records (EHRs), is an important challenge, which can enhance the reliability and usability of such records. Inconsistencies in such records may lead to confusion and mistakes and may result in spurious conclusions of applications that utilize these data. For example inconsistencies in noting drug prescription in EHR can lead to disastrous results in patient care.

One issue in Electronic Records (ER) design is balancing between the high expressive power of storing data in a non-structured field, such as free-text fields, versus the benefits of using structured fields, such as coded fields, where a code is chosen from a predefined list. While the use of non-structured field facilitates rapid and relatively convenient data entry, using structured field can enhance ER retrieval, mining, and analysis, and may improve communication between different consumers of the records. Many ER implementations therefore rely on both methods.

BRIEF SUMMARY

One exemplary embodiment of the disclosed subject matter is a computer-implemented method comprising: automatically determining, by a computer, inconsistencies between fields in electronics records, the fields comprise at least a structured field and a non-structured field, the fields are designed to be able to include overlapping information in structured and non-structured form; and indicating, by the computer, to a user potential inconsistencies.

Another exemplary embodiment of the disclosed subject matter is a computerized apparatus having a processor coupled with a memory unit, the processor being adapted to perform the steps of: automatically determining, by a computer, inconsistencies between fields in electronics records, the fields comprise at least a structured field and a non-structured field, the fields are designed to be able to include overlapping information in structured and non-structured form; and indicating, by the computer, to a user potential inconsistencies.

Yet another exemplary embodiment of the disclosed subject matter is a computer program product comprising a non-transitory computer readable medium retaining program instructions, which instructions when read by a processor, cause the processor to perform the steps of: automatically determining, by a computer, inconsistencies between fields in electronics records, the fields comprise at least a structured field and a non-structured field, the fields are designed to be able to include overlapping information in structured and non-structured form; and indicating, by the computer, to a user potential inconsistencies.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
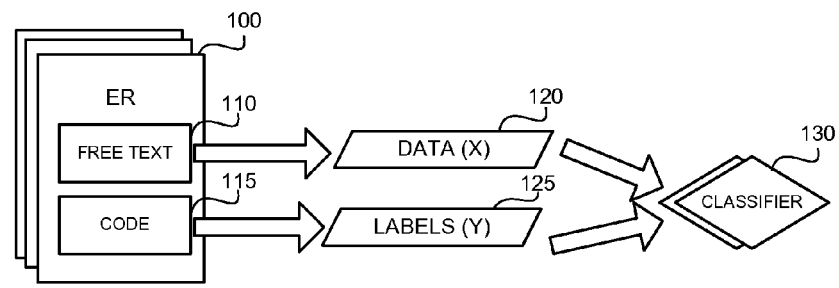
FIG. 1 shows an illustration of a flow of operation in a computerized environment, in accordance with some exemplary embodiments of the disclosed subject matter.
Figure 1:
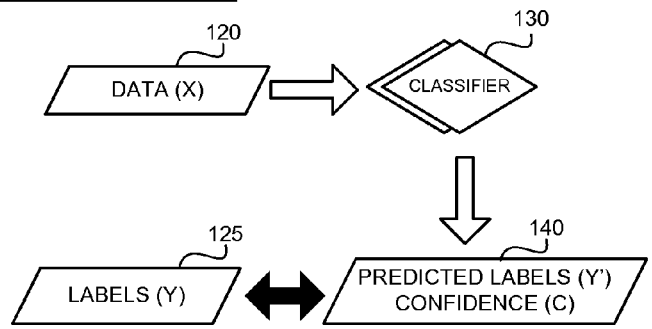

The disclosed subject matter is described below with reference to flowchart illustrations and/or block diagrams of methods, apparatus (systems) and computer program products according to embodiments of the subject matter. It will be understood that blocks of the flowchart illustrations and/or block diagrams, and combinations of blocks in the flowchart illustrations and/or block diagrams, can be implemented by computer program instructions. These computer program instructions may be provided to one or more processors of a general purpose computer, special purpose computer, a tested processor, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a non-transient computer-readable medium that can direct a computer or other programmable data processing apparatus to function in a particular manner, such that the instructions stored in the non-transient computer-readable medium produce an article of manufacture including instruction means which implement the function/act specified in the flowchart and/or block diagram block or blocks.

The computer program instructions may also be loaded onto a device. A computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

One technical problem dealt with the disclosed subject matter is to automatically detect inconsistencies in ER between overlapping structured and non-structured fields. In a single ER there may be fields that are overlapping, in the sense that they may provide the same information. As such overlapping may exist, the information that each field provide may be inconsistent.

As an example, in a EHR, a free-text field may be used to indicate the symptoms, while a coded field may be used to indicate the most noticeable symptoms. As another example, the gender and age of the patient may appear in both a structured and non-structured fields of the EHR. In ER for car accident claims, the accident may be described in a free text, while the damage may be indicated in structured fields (e.g., damage to windshield?, damage to wheels?, etc.). As yet another example, an ER recording summary of a consult with a consultant (such as financial advisor, pension advisor, real estate agent, or the like), may indicate the client's wishes and understandings with the consultant in free text, and the decision how to act on these may a code describing the chosen course. As yet another example, surveys, such as customer service surveys, where the customer ticks the level of his satisfaction from different aspects and can then describes his experience in free text, may introduce overlapping fields of both structured and non-structured data.

It will be noted that between the overlapping fields there may be a relation of one structured field to many non-structured fields (e.g., same information provided by the code can be represented in several free-text fields), a relation of one non-structured field to many structured fields (e.g., the free text may summarize information of several codes), a relation of many-to-many, or the like.

One technical solution provided by the disclosed subject matter is to utilize machine learning prediction mechanism to automatically predict the structured data based on the non-structured data and in cases where the prediction is inconsistent with the data in the structured data, indicate the inconsistency. The indication may be provided to a user for inspection, such as by highlighting or otherwise indicating using a visual cue or non-visual cue to the user the inconsistency.

In some exemplary embodiments, for each non-structured field that hold information overlapping with that captured by a structured field, one or more machine learning classifiers may be trained to predict the code using the ERs. The trained classifiers may be used to provide a prediction of the structured field of the ERs.

In some exemplary embodiments, the disclosed subject matter may have no clear distinction between the training and test data. The same ERs may be used for both the training phase of the classifiers and the prediction.

In some exemplary embodiments, as the ERs used for training may be assumed to have inconsistent and therefore wrong data, some of the ERs may be removed from the training set. In some exemplary embodiments, the removed ERs may be used during the prediction phase in order to provide indication in case it is still determined that the data in the removed ERs is inconsistent.

In some exemplary embodiments, the predicted structured data and the actual structured data in the ER may be compared. In case the prediction is inconsistent with the actual data in the ER, the confidence measurement of the classifier may be used to determine whether or not to indicate the ER as inconsistent. In some exemplary embodiments, in case the confidence in the prediction is above a threshold confidence the indication may be provided. Additionally or alternatively, an inconsistency confidence, measured based on the confidence of the classifier in choosing the non-predicted actual data, may be used. The ER may be considered inconsistent only in case the inconsistency confidence is above a predetermined threshold.

As an example, consider a case in which the alternative options are $L_1$, $L_2$, $L_3$, $L_4$. The classifier may predict $L_1$, while the actual data may be $L_2$ (i.e., the ER may indicate $L_2$). The classifier may provide confidence measurement for each option, denoted as $C_i$. As an example, the confidence measurements may be $C_1=0.4$, $L_2=0.01$, $L_3=0.3$, $L_4=0.29$. In some exemplary embodiments, the confidences may be summed to exactly 100% ($\Sigma\ C_i=1$). As can be appreciated from the aforementioned example, while the confidence in the prediction may be low, the confidence that the data in the ER is inconsistent may be high. In this example, the confidence in the prediction is 40% ($C_1$) while the inconsistency confidence is 99% (100%-$C_2$).

In some exemplary embodiments, the structured data may be abstracted to groups representing a set of separate options. As an example only, consider the structured field indicating a specific disease. It may be the case that differentiating between specific forms of Cancer may not be feasible for a classifier. Instead all forms of Cancer may be grouped as a single abstract structured data "Cancer", which does not appear in any ER and the classifier may predict whether for non-structured data the disease should be "Cancer" or another disease, such as lupus. Similarly, an age structured data which may receive any number may be abstracted into several age groups such as infant (0-2), child (3-11), teenager (12-19), young adult (20-29), adult (30-59), mature (60-79) and elderly (80 or higher). Other grouping may be performed of different sets of valuations to the structured data field.

One technical effect is enabling automatic inconsistencies detection and thereby improving the quality of the data. Additionally, cleansing the data from inconsistencies may improve the results of data mining applications, leading to higher quality insights. Specifically, in the health care domain, where free text and codes are both prevalent, and mistakes are fatal, this ability can be crucial.

Another technical effect is automatically identifying potential fraudulent behavior, by identifying inconsistencies that may be introduced intentionally in an attempt to defraud, such as filing fraudulent reimbursement or insurance claims.

Yet another technical effect is the surprising effect of using the same data as training data and data to be predicted. Even though that in some embodiments the same data is used for training and for prediction, discrepancies may still be deduced by avoiding over-fitting of the classifiers to the training data.

In some exemplary embodiments, a task of detecting inconsistencies is an unsupervised learning task which does not rely on having a training dataset. The disclosed subject matter may enable performing the unsupervised learning task by creating a supervised task. The supervised task using the same data received for the unsupervised task both for training and as input for prediction by the supervised task.

Furthermore, in some embodiments, a portion of the data may be indicated as inconsistent and not used for the training phase. However, the same potentially inconsistent data may be determined automatically by the disclosed subject matter to be consistent, such as a rare instance. Although a first filtering process may be performed, the same data may still be used in a prediction phase and based on inconsistency confidence be determined to be consistent with the non-structured data.

Referring now to FIG. 1 showing an illustration of a flow of operation in a computerized environment, in accordance with some exemplary embodiments of the disclosed subject matter. FIG. 1 shows a Training Phase and an Inconsistency Detection Phase.

ERs 110 may include overlapping structured fields, such as Code 115, and non-structured fields, such as Free Text 110. Based on Free Text 110, Data 120, also denoted as X, may be generated, such as for example, a set of words used in the free text. Labels associated with each instance, also denoted as Y, may be generated based on Code 115. In some exemplary embodiments, several distinct codes may be grouped and represented using a single label.

In the training phase, one or more Classifiers 130 may be trained based on Data 120 and Labels 125. In some exemplary embodiments, over-fitting may be avoided by using a cross validation scheme. One possible cross validation scheme may be to divide the classifiers into groups and train each group based on a different portion of Data 120 and Labels 125.

The trainer Classifiers 130 may be used in the Inconsistency Detection Phase to provide Prediction Information 140. Prediction Information 140 may comprise predicted labels, also denoted as Y', for each instance of Data 120. Additionally or alternatively, Prediction Information 140 may further comprise confidence measurements of the predicted label and of additional non-predicted labels.

The disclosed subject matter may detect inconsistencies between Labels 125 and predicted labels. In some exemplary embodiments, in order to avoid a substantial number of false positive instances (i.e., instances in which inconsistency is indicated, but the indication is wrong), confidence measurements may be used to determine which inconsistencies to report. As an example, inconsistency confidence may be computed and based thereon, such as above a predetermined threshold (e.g., 50%, 60% or the like), it may be determined whether or not to report the inconsistency. In some exemplary embodiments, confidence in the prediction may be used as well. Additionally or alternatively, both inconsistency measurements may be used in combination. As an example only, inconsistency may be reported in case the inconsistency confidence is above a first threshold or the confidence in the prediction is above a second threshold. As another example, the inconsistency may be reported in case the inconsistency confidence is above a first threshold or in case the inconsistency confidence is above and second threshold and the confidence in the prediction is above a third threshold. Other combinations of these and similar parameters may also be used.

Based on inconsistencies detected, a report or indication may be provided to the user.

Figure 2:
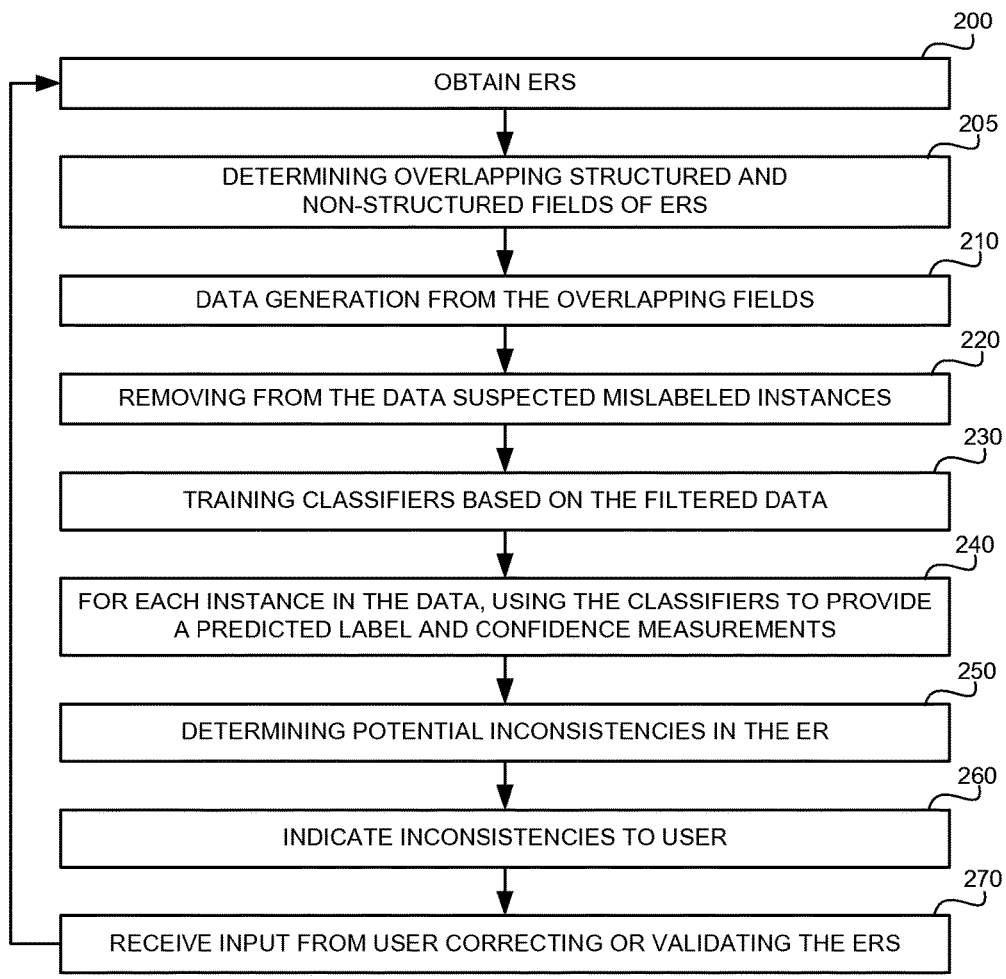
FIG. 2 shows a flowchart diagram of steps in a method, in accordance with some exemplary embodiments of the disclosed subject matter.

Referring now to FIG. 2 showing a flowchart diagram of steps in a method, in accordance with some exemplary embodiments of the disclosed subject matter.

In Step 200, ERs may be obtained. The ERs may be obtained from an electronic data storage unit, a database, a remote computerized apparatus, or the like.

In Step 205, overlapping structured and non-structured fields in the ERs may be determined. In some exemplary embodiments, a user may indicate overlapping relationships between fields. In some exemplary embodiments, the relationship may be one-to-one, many-to-many, many-to-one, or the like. For simplicity, the method is described while addressing a one-to-one relationship. However, the disclosed subject matter is not limited to such a case.

In Step 210, pairs of data (x) and labels (y) may be generated from the overlapping fields. In some exemplary embodiments, structured fields may be used to generate labels, while non-structured fields may be used to generate data.

In some exemplary embodiments, the content of the non-structured field may be modeled to allow Natural Language Processing (NLP), such as, for example, using a Bag of Words (BoW) model. Other modeling for NLP purposes may also be applicable.

In some exemplary embodiments, Mapping from structured field to labels may be performed using one to one mapping, many to one mapping, or the like. In the many to one mapping, distinct values of structured fields may be aggregated into a smaller set of labels. In some exemplary embodiments, many to one mapping may be used when there is not enough information in the non-structured field to properly differentiate between all values of the structured field, or when not enough instances are observed for some of the values of the structured field.

In Step 220, suspected mislabeled instances may be removed. In some exemplary embodiments, the data used for training may be assumed to include inconsistencies, implying that for some instances in the training set, the label is incorrect. These mislabeled instances may decrease the prediction accuracy of the classifiers, even if they occur in a small fraction of the data. In some exemplary embodiments, such suspected mislabeled ERs may be removed from the data used for training purposes. In some exemplary embodiments, Step 220 may be performed by performing a first round of training and classification, and then remove all instances for which all classifiers predict with high confidence (e.g., confidence above a predetermined threshold) a label different from the actual label in the ER. The filtered training data may be used in Step 230 for training the classifiers. Additionally or alternatively, the training may be performed using all the instances without a-priori filtering them.

In Step 240, for each instance in the data, the classifiers may be used to predict a label for the data. In some exemplary embodiments, confidence measurement in each predicted and not predicted label may be determined, such as an estimated probability of correct prediction. Confidence measurements may be provided by the classifier as an inherent property thereof (such as, for example, using the posterior probability of the most probable class (MAP) for a Naive Bayes classifier), using direct methods to estimate confidence, or using other methods.

It will be noted that Step 240 may be performed with respect to all ERs including those instances removed in Step 220.

In Step 250, potential inconsistencies in the ER may be determined. The predicted label and the actual label of the ER may be compared and in case they are different it may be determined as a potential inconsistency. In some exemplary embodiments, in order to avoid indicating too many false positives, only a portion of the instances in which there is a difference may be considered as potential inconsistencies. In some exemplary embodiments, inconsistency confidence and/or confidence measurements may be used to determine whether the different prediction is considered as inconsistency.

In some exemplary embodiments, inconsistencies may be determined based on a quorum decision by all the classifiers, by a majority of the classifiers, or the like.

In some exemplary embodiments, it may be sufficient that a single classifier may determine with an inconsistency confidence above a predetermined threshold, that the instance is inconsistent in order to be determined as a potential inconsistency. Such may be the case in situations where errors may be expensive or fatal, such as in EHRs. Additionally or alternatively, in order for an instance to be considered as inconsistent, it may be required that several, majority or all of the classifiers indicate potential mislabeling and optionally with inconsistency confidence above a threshold or other confidence-related constraints. Such may be the case in scenarios where mislabeling is not considered as expensive or in cases where it is desired to reduce probability of false positive indications at the expense of increasing probability of false negatives (e.g., not indicating a mislabeling).

In Step 260, determined inconsistencies of Step 250 may be indicated to the user. The inconsistencies may be indicated using a report, by providing a visual or other cue to the user, or the like.

In Step 270, input received from the user may be used to correct the ER or validate the information in the ER (e.g., indicate of a false positive detection).

In some exemplary embodiments, the method may be repeated using new ERs. In some exemplary embodiments, the ERs of the previous iterations may be used. In some exemplary embodiments, and in view of the human validation, ERs manually verified may not be removed in Step 220 even though they might be suspected as mislabeled.

Figure 3:
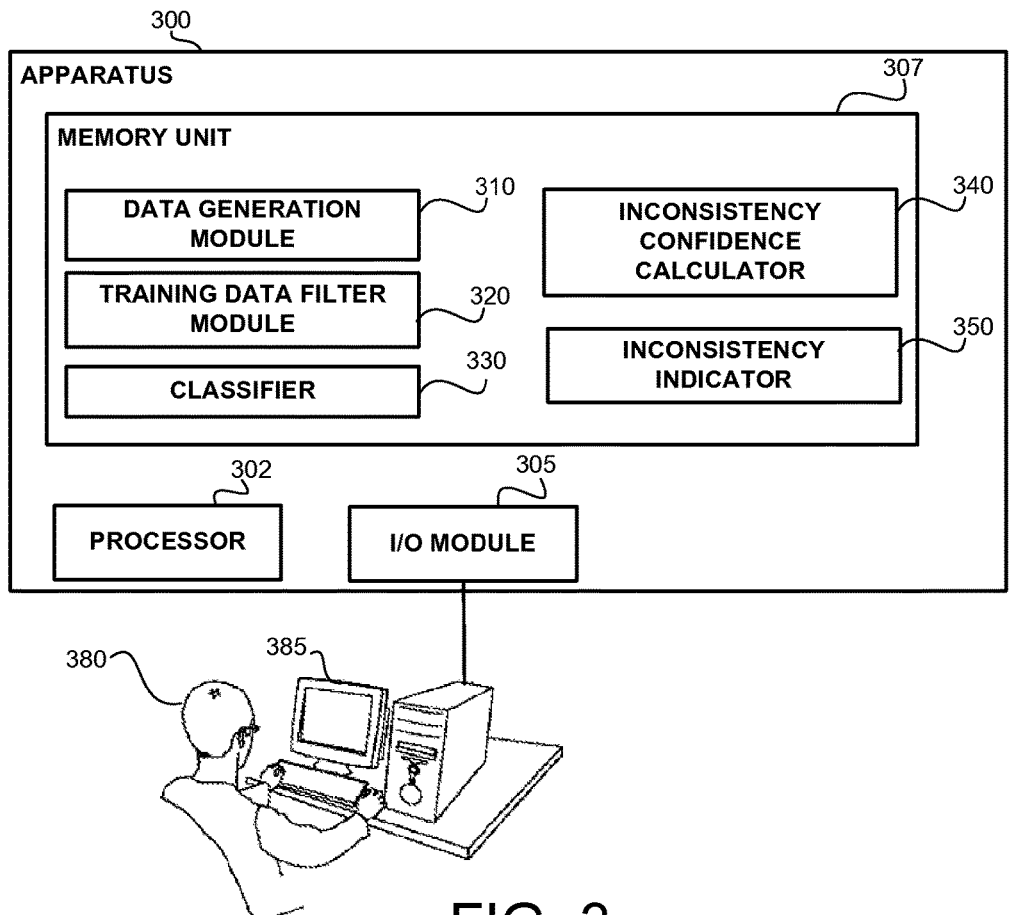
FIG. 3 shows a block diagram of components of an apparatus, in accordance with some exemplary embodiments of the disclosed subject matter.

Referring now to FIG. 3 showing a block diagram of components of an apparatus, in accordance with some exemplary embodiments of the disclosed subject matter. An apparatus 300 may be a computerized apparatus adapted to perform methods such as depicted in FIGS. 1, 2.

In some exemplary embodiments, Apparatus 300 may comprise a Processor 302. Processor 302 may be a Central Processing Unit (CPU), a microprocessor, an electronic circuit, an Integrated Circuit (IC) or the like. Alternatively, Apparatus 300 can be implemented as firmware written for or ported to a specific processor such as Digital Signal Processor (DSP) or microcontrollers, or can be implemented as hardware or configurable hardware such as field programmable gate array (FPGA) or application specific integrated circuit (ASIC). The processor 302 may be utilized to perform computations required by Apparatus 300 or any of it subcomponents.

In some exemplary embodiments of the disclosed subject matter, Apparatus 300 may comprise an Input/Output (I/O) Module 305 such as a terminal, a display, a keyboard, an input device or the like to interact with the system, to invoke the system and to receive results. It will however be appreciated that the system can operate without human operation.

In some exemplary embodiments, the I/O Module 305 may be utilized to provide an interface to a User 380 which may utilize a Man-Machine Interface (MMI) 385 to interact with Apparatus 300, such as by indicating overlapping fields, correcting inconsistencies or validating the content of an ER, or the like.

In some exemplary embodiments, Apparatus 300 may comprise a Memory Unit 307. Memory Unit 307 may be persistent or volatile. For example, Memory Unit 307 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, Memory Unit 307 may retain program code operative to cause Processor 302 to perform acts associated with any of the steps shown in FIGS. 1 and 2.

The components detailed below may be implemented as one or more sets of interrelated computer instructions, executed for example by Processor 302 or by another processor. The components may be arranged as one or more executable files, dynamic libraries, static libraries, methods, functions, services, or the like, programmed in any programming language and under any computing environment.

Data Generation Module 310 may be configured to generate data and labels based upon ERs.

Training Data Filter Module 320 may be configured to remove instances suspected of being mislabeled from a training set prior to using the training set to train Classifier 330.

Classifier 330 may be any module capable of providing a prediction of a label Y based on data X. In some exemplary embodiments, Classifier 330 may be configured to be trained using a training set of pairs (X,Y). In some exemplary embodiments there may be a plurality of Classifiers each based on a different supervised learning mechanism to provide a prediction for an instance. Classifier 330 may be, for example, a Naive Bayes classifier, a Quadratic classifier, Support Vector Machine-based classifier, linear classifier, or the like. In some exemplary embodiments, Classifier 330 may be configured to provide confidence measurement for the predicted label and/or alternative and non-predicted labels.

Inconsistency Confidence Calculator 340 may be configured to compute inconsistency confidence. In some exemplary embodiments, the inconsistency confidence by determining actual label according to ER, obtaining confidence in a prediction of the actual label and computing one minus the obtained confidence measurement.

Inconsistency Indicator 350 may be configured to provide indications to the user of suspected inconsistent records. The indications may be provided, for example, by a report, by highlighting fields, by providing other types of visual cues to the user, or the like.

Figure 4:
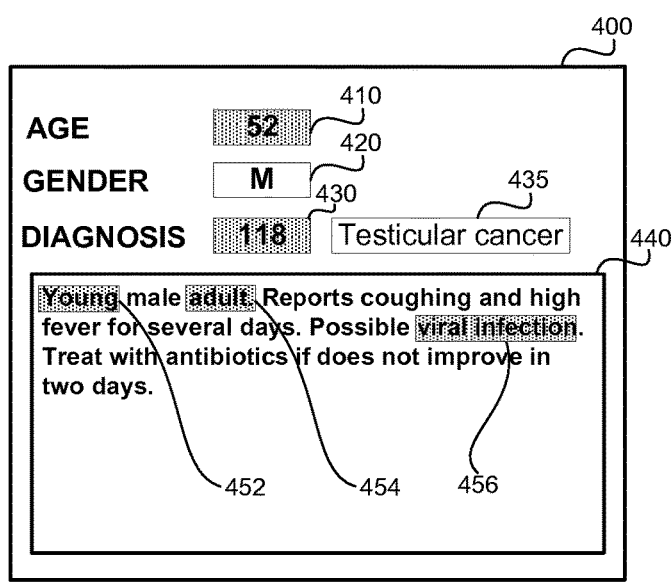
FIG. 4 shows an illustration of a form indicating an inconsistent ER, in accordance with some exemplary embodiments of the disclosed subject matter.

Referring now to FIG. 4 showing an illustration of a form indicating an inconsistent ER, in accordance with some exemplary embodiments of the disclosed subject matter.

Form 400 may represent an ER comprising both structured and non-structured fields. Age, Gender and Diagnosis may be provided as structured fields 410, 420, 430. The code for the diagnosis may be translated to phrase in display field 435. Free text field 440 may be used to provide non-structured data.

In response to determining that the free text and the codes are inconsistent, such as in view of the age being 52 while the text describing young adult, and in view of the diagnosis being associated with cancer while the text referring to viral infection visual cues may be provided to the user to indicate the inconsistencies.

In some exemplary embodiments, the inconsistent code fields may be highlighted, such as field 410 and 430. Additionally or alternatively, the free text field 440 may also be highlighted in its entirety to indicate the inconsistency. Additionally or alternatively, only portion of the free text may be highlighted, such as words that are the cause of the different prediction. As an example, highlighting 452, 454 and 456 may be provided. In some exemplary embodiments, different colors may be used to correlate between indications of overlapping fields such as in case there are several inconsistencies in the same ER, resulting from different fields or different portions of fields. As an example only, highlights 452 and 454 may be provided in one visual manner similar to that of field 410 while highlight 456 may be provided in a second visual manner similar to that of filed 430.

The flowchart and block diagrams in the figures illustrate the architecture, functionality, and operation of possible implementations of systems, methods and computer program products according to various embodiments of the present disclosure. In this regard, each block in the flowchart and some of the blocks in the block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, any non-transitory computer-readable medium, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A computer-implemented method comprising:
  automatically determining, by a computer, inconsistencies between fields in electronic records, the fields comprise at least a structured field and a non-structured field, the fields are designed to be able to include overlapping information in structured and non-structured form, wherein said automatically determining comprises:
    obtaining one or more groups of fields of the electronic records, each of which groups comprising at least one structured field and at least one non-structured field, wherein the fields in each group have an overlapping relationship;
    generating instances of pairs of data and a corresponding actual label from the electronic records based on the fields in each group, wherein the data is defined using a value of the non-structured field of an electronic record, wherein the actual label is defined using a value of the structured field of the electronic record and a mapping between values of the structured field and a set of labels;
    for each classifier of one or more classifiers:
      training the classifier based on the instances;
      predicting by the classifier predicted labels for each instance of the instances, whereby a predicted label is predicted by a classifier for an instance which was used to train the classifier; and
      comparing the predicted label with the actual label; and
  indicating potential inconsistencies, by the computer, to a user.

2. The computer-implemented method of claim 1, wherein said automatically determining further comprises: computing an inconsistency confidence based on a confidence in predicting the actual label, and determining an inconsistency in response to the inconsistency confidence being above a predetermined threshold.

3. The computer-implemented method of claim 1, wherein the one or more classifiers comprise a plurality of classifiers, wherein a determination of an inconsistency is based on a prediction by the plurality of classifiers and based on weighing results from the plurality of classifiers.

4. The computer-implemented method of claim 1, wherein said training is based on a portion of the instances, wherein the portion excludes instances suspected of being mislabeled, and wherein said predicting is performed with respect to the instances, including the instances excluded from the portion.

5. The computer-implemented method of claim 1, wherein said automatically determining comprises determining two inconsistencies in a same electronic record, wherein said indicating is by visual cues when displaying the electronic record to the user, wherein a first inconsistency is indicated by using a first visual cue for each of a first pair of fields that are determined to comprise the first inconsistency, wherein a second inconsistency is indicated by using a second visual cue for each of a second pair of fields that are determined to comprise the second inconsistency, wherein the first and second visual cues are visually different.

6. The computer-implemented method of claim 1 further comprises receiving from the user input modifying the inconsistent fields or validating content thereof.

7. The computer-implemented method of claim 1, wherein the structured field is a field comprising a value selectable from a predetermined set of values, and wherein the non-structured field is a field comprising free text input.

8. The computer-implemented method of claim 1, wherein a non-structured field in the electronic records is capable of comprising information that overlaps a first structured field and a second structured field, wherein said generating comprises generating, for each electronic record, a first instance based on values of the non-structured field and of the first structured field and a second instance based on values of the non-structured field and of the second structured field, whereby two or more instances are generated based on a same electronic record.

9. The computer-implemented method of claim 1, wherein the mapping is a many to one mapping.

10. A computerized apparatus having a processor coupled with a memory unit, the processor being adapted to perform the steps of:
  automatically determining, by a computer, inconsistencies between fields in electronic records, the fields comprise at least a structured field and a non-structured field, the fields are designed to be able to include overlapping information in structured and non-structured form, wherein said automatically determining comprises:
    obtaining one or more groups of fields of the electronic records, each of which groups comprising at least one structured field and at least one non-structured field, wherein the fields in each group have an overlapping relationship;
    generating instances of pairs of data and a corresponding actual label from the electronic records based on the fields in each group, wherein the data is defined using a value of the non-structured field of an electronic record, wherein the actual label is defined using a value of the structured field of the electronic record and a mapping between values of the structured field and a set of labels;
    for each classifier of one or more classifiers:
      training the classifier based on the instances;
      predicting by the classifier predicted labels for each instance of the instances, whereby a predicted label is predicted by a classifier for an instance which was used to train the classifier; and
      comparing the predicted label with the actual label; and
    indicating potential inconsistencies, by the computer, to a user.

11. The computerized apparatus of claim 10, wherein said automatically determining further comprises: computing an inconsistency confidence based on a confidence in predicting the actual label, and determining an inconsistency in response to the inconsistency confidence being above a predetermined threshold.

12. The computerized apparatus of claim 10, wherein the one or more classifiers comprise a plurality of classifiers, wherein a determination of an inconsistency is based on a prediction by the plurality of classifiers and based on weighing results from the plurality of classifiers.

13. The computerized apparatus of claim 10, wherein said training is based on a portion of the instances, wherein the portion excludes instances suspected of being mislabeled, and wherein said predicting is performed with respect to the instances, including the instances excluded from the portion.

14. The computerized apparatus of claim 10, wherein said automatically determining comprises determining two inconsistencies in a same electronic record, wherein said indicating is by visual cues when displaying the electronic record to the user, wherein a first inconsistency is indicated by using a first visual cue for each of a first pair of fields that are determined to comprise the first inconsistency, wherein a second inconsistency is indicated by using a second visual cue for each of a second pair of fields that are determined to comprise the second inconsistency, wherein the first visual cue and the second visual cue are visually different.

15. The computerized apparatus of claim 10 further comprises receiving from the user input modifying the inconsistent fields or validating content thereof.

16. The computerized apparatus of claim 10, wherein the structured field is a field comprising a value selectable from a predetermined set of values, and wherein the non-structured field is a field comprising free text input.

17. A computer program product comprising a non-transitory computer readable medium retaining program instructions, which instructions when read by a processor, cause the processor to perform the steps of:
  automatically determining, by a computer, inconsistencies between fields in electronic records, the fields comprise at least a structured field and a non-structured field, the fields are designed to be able to include overlapping information in structured and non-structured form, wherein said automatically determining comprises:
    obtaining one or more groups of fields of the electronic records, each of which groups comprising at least one structured field and at least one non-structured field, wherein the fields in each group have an overlapping relationship;
    generating instances of pairs of data and a corresponding actual label from the electronic records based on the fields in each group, wherein the data is defined using a value of the non-structured field of an electronic record, wherein the actual label is defined using a value of the structured field of the electronic record and a mapping between values of the structured field and a set of labels;

for each classifier of one or more classifiers:
  training the classifier based on the instances;
  predicting by the classifier predicted labels for each instance of the instances, whereby a predicted label is predicted by a classifier for an instance which was used to train the classifier; and
comparing the predicted label with the actual label; and
indicating potential inconsistencies, by the computer, to a user.

18. The computer program product of claim 17, wherein said automatically determining further comprises: computing an inconsistency confidence based on a confidence in predicting the actual label, and determining an inconsistency in response to the inconsistency confidence being above a predetermined threshold.

19. The computer program product of claim 17, wherein said training is based on a portion of the instances, wherein the portion excludes instances suspected of being mislabeled, and wherein said predicting is performed with respect to the instances, including the instances excluded from the portion.

* * * * *